US00PP13658P29

(12) United States Plant Patent
Olesen et al.

(10) Patent No.: US PP13,658 P2
(45) Date of Patent: Mar. 18, 2003

(54) MINIATURE ROSE PLANT NAMED 'POULMOON'

(75) Inventors: L. Pernille Olesen; Mogens N. Olesen, both of Fredensborg (DK)

(73) Assignee: Poulsen Roser ApS, Fredensborg (DK)

( * ) Notice: Subject to any disclaimer, the term of this patent is extended or adjusted under 35 U.S.C. 154(b) by 0 days.

(21) Appl. No.: 09/136,896

(22) Filed: Aug. 18, 1998

(51) Int. Cl.[7] ..... A01H 5/00

(52) U.S. Cl. ..... Plt./118; Plt./125

(58) Field of Search ..... Plt./118, 125

(56) References Cited

PUBLICATIONS

UPOU–ROM, Plant Variety Database, GTI Jouve Retrieval Software, 2 citat ions for 'Poulmoon'.*

Community Plant Variety Office "Certificate on the Grant . . ." 6 pages. Jul. 20, 1998.

Candian Food Inspection Agency "Applications Accepted for filing" Plant Varieties Journal 1 page. Oct. 1997.

* cited by examiner

*Primary Examiner*—Howard J. Locker

(57) ABSTRACT

A new miniature rose plant which has abundant yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between 'POULemon' and an unnamed seedling. The two parents were crossed and the resulting seeds were planted in a controlled environment. The new variety is named 'POULmoon'.

The new rose may be distinguished from its seed parent, 'POULemon', by the following combination of characteristics:

1. 'POULemon' has whitish-yellow flowers, while 'POULmoon' has soft yellow flowers.

2. 'POULmoon' has greater lastingness than 'POULemon'.

3. 'POULmoon' has thicker and glossier foliage, and is easier to propagate than 'POULemon'.

The new variety may be distinguished from its pollen parent, an unnamed seedling, created by the same inventors, by the following combination of characteristics:

1. The parents of the unnamed seedling are 'Mini-Poul', a red-yellow bi-color rose, and a bright yellow Patio rose.

2. The unnamed seedling has yellow flowers with red intonations, while 'POULmoon' has soft yellow flowers.

The objective of the hybridization of this rose variety for commercial greenhouse culture was to create a new and distinct variety with unique qualities, such as:

1. Uniform and abundant soft yellow flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities was not present in previously available commercial cultivars of this type and distinguish 'POULmoon' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULmoon' was selected by the inventors as a single plant from the progeny of the hybridization in April, 1994.

Asexual reproduction of 'POULmoon' by cuttings and traditional budding was first done by L. Pernille and Mogens N. Olesen in their nursery in Fredensborg, Denmark in June, 1994. This initial and other subsequent propagations conducted in controlled environments have demonstrated that the characteristics of 'POULmoon' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULmoon'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULmoon', as observed in its growth in glasshouses in Fredensborg, Denmark; Burlington, Canada, and in a field nursery in Applegate, Jackson County, Oreg. Color references are made using The Royal Horticultural Society (London, England) Colour Chart, 1995; except where common terms of color are used.

For a comparison, the nearest existing rose variety is 'POULsun', a patented variety by the same inventors described and illustrated in U.S. Plant Pat. No. 9,716 and issued on Dec. 3, 1996. Chart 1 details several physical characteristics of 'POULmoon' and 'POULsun'.

CHART 1

| | 'POULmoon' | 'POULsun' |
|---|---|---|
| Petal, color of upper surface | Yellow Group 4C and 6C | Yellow Group 13A |
| Petal, color of reverse surface | Yellow Group 4C and 6D | Yellow Group 13B |
| Petalage | 35–40 petals | 30–35 petals |

Parents: 'POULemon'×unnamed seedling.
Classification:
*Botanical.*—*Rosa hybrida.*
*Commercial.*—Miniature.

FLOWER AND FLOWER BUD

Blooming habit: Recurrent.
Flower bud:
*Size.*—Upon opening, 35 mm–45 mm in length from base of receptacle to end of bud.
*Bud form.*—Globular.
*Bud color.*—As sepals unfold and at ¼ opening Yellow Group 6C.
*Sepals.*—Green Group 137B. Some tips of sepals with intonations of Red-Greyed Group 179A. Weak foliaceous appendages and stipitate glands on three of the five sepals. Surfaces of other sepals slightly pubescent.
*Receptacle.*—Surface: Smooth, glabrous. Shape: Broadly urn-shaped. Size: Medium to large. 5 mm (h)×8 mm (w). Color: Green Group 138A–138B.
*Peduncle.*—Surface: Moderate numbers of stipitate glands. Length: 35–50 mm average length. Color: Green Group 137C. Strength: Erect.
*Borne.*—Generally with 1–2 buds per flowering stem.
Flower bloom:
*Size.*—Medium size for a 13 cm pot rose. Average flower diameter is 45–55 mm when open.
*Form.*—Shape of flower when viewed from the side: Upon opening, upper part: Flattened convex. Upon opening, lower part: Flattened convex. Open flower, upper part: Flat to flattened convex. Open flower, lower part: Concave.
*Petalage.*—Double to very double. Average range: 34–40 under normal conditions with approximately 5–10 petaloids.
Color:
*Upon opening.*—Petals: Upper Surface: Yellow Group 6C. Reverse Side: Yellow Group 6D. Some exterior petals with intonation of Yellow-Green 145B. Basal petal spots: Present. Small. Outer Side: Yellow Group 3C. Inner Side: Yellow Group 3C.
*After opening.*—Outermost petals: Upper Surface: Yellow Group 4C. Reverse Side: Yellow Group 4C. Innermost petals: Upper Surface: Yellow Group 6C. Reverse Side: Yellow Group 6D. Basal petal spots: Outer Side: Yellow Group 3D. Inner Side: Yellow Group 3D.
General tonality: On open flower, Yellow Group 6C. No change in the general tonality at the end of the second day. Afterwards, general tonality is Yellow Group 5C.
Petals:
*Petal edge.*—With small point in center of margin.
*Petaloids.*—Present. Quantity 5–10.
*Fragrance.*—Light floral scent.
*Duration.*—As a pot plant, flowers last from 8 to 10 days. As a cut flower 5 to 7 days.
*Thickness.*—Average.
*Shape.*—Outermost petals rounded. Innermost petals oblong.
*Form.*—Flat.
*Arrangement.*—Regular.
Reproductive organs:
*Pollen.*—Color: Yellow-Orange 17A–22A. Abundance: Average.
*Anthers.*—Size: Medium. Color: Yellow Group 13B. Abundance: Average.
*Filaments.*—Color: Yellow-Green Group 154C.
*Stigmas.*—Superior in location to anthers. Color: Green-Yellow Group 1C.
*Styles.*—Color: Green-White Group 157A. Some intonations of Red-Purple Group 57D in upper portion of style.

PLANT

Plant growth: Vigorous, compact, upright to bushy. When grown as a 13 cm pot plant, the average height of the plant itself is 20 to 22 cm and the average width is 18 to 20 cm. When grown as a nursery plant (on its own roots) the average plant height is 50–65 cm and the average plant width is 45–55 cm.
Stems:
*Color.*—Young wood: Green Group 143A. Older wood: Green Group 143A–138A.
*Thorns.*—Incidence: Few thorns. Some stems nearly thornless. Others with 7–9 thorns per 10 cm of stem. Size: Average length: 3 mm–5 mm. Color: Green-White Group 157B when young. Older thorns, Greyed-Orange Group 174C. Shape: Linear.
*Surface.*—Young wood: Smooth. Older wood: Smooth.
Plant foliage: Normal number of leaflets on normal leaves in middle of the stem: 5–7 leaflets.
*Leaf size.*—Small to medium. 65 mm (l)×40 mm (w).
*Abundance.*—Less than average.
*Color.*—Upper Leaf Surface: Green Group 137A. Lower Leaf Surface: Green Group 137B. Upper leaf surface Group 137B–C. Lower leaf surface Green Group 137C. Both upper and lower leaflet margins and distal margins of sepals with intonation of Greyed-Red Group 179A.
Plant leaves and leaflets:
*Stipules.*—Present. Size: 6 mm–8 mm. Color: Green Group 137B.
*Petiole.*—Length: 10 mm–15 mm. Color: Green Group 137B. Margins: With moderate number of stipitate glands. Prickles: None.
*Rachis.*—Color: Green Group 137B. Underneath: With small prickles.
*Leaflet.*—Edge: Serrated. Shape: Ovate.
*Other.*—Moderately glossy surface. Thin texture.

Disease resistance: Above average resistance to mildew and Botrytis under normal growing conditions in Fredensborg, Denmark, and Burlington, Canada.

We claim:

1. A new and distinct variety of rose plant of the miniature class, substantially as herein illustrated and described as a distinct and novel rose variety due to its abundant, soft yellow flowers, vigorous and compact growth, year round flowering under glasshouse conditions, suitability for production from softwood cuttings in pots, and durable flowers and foliage which make the variety suitable for distribution in the floral industry.

* * * * *

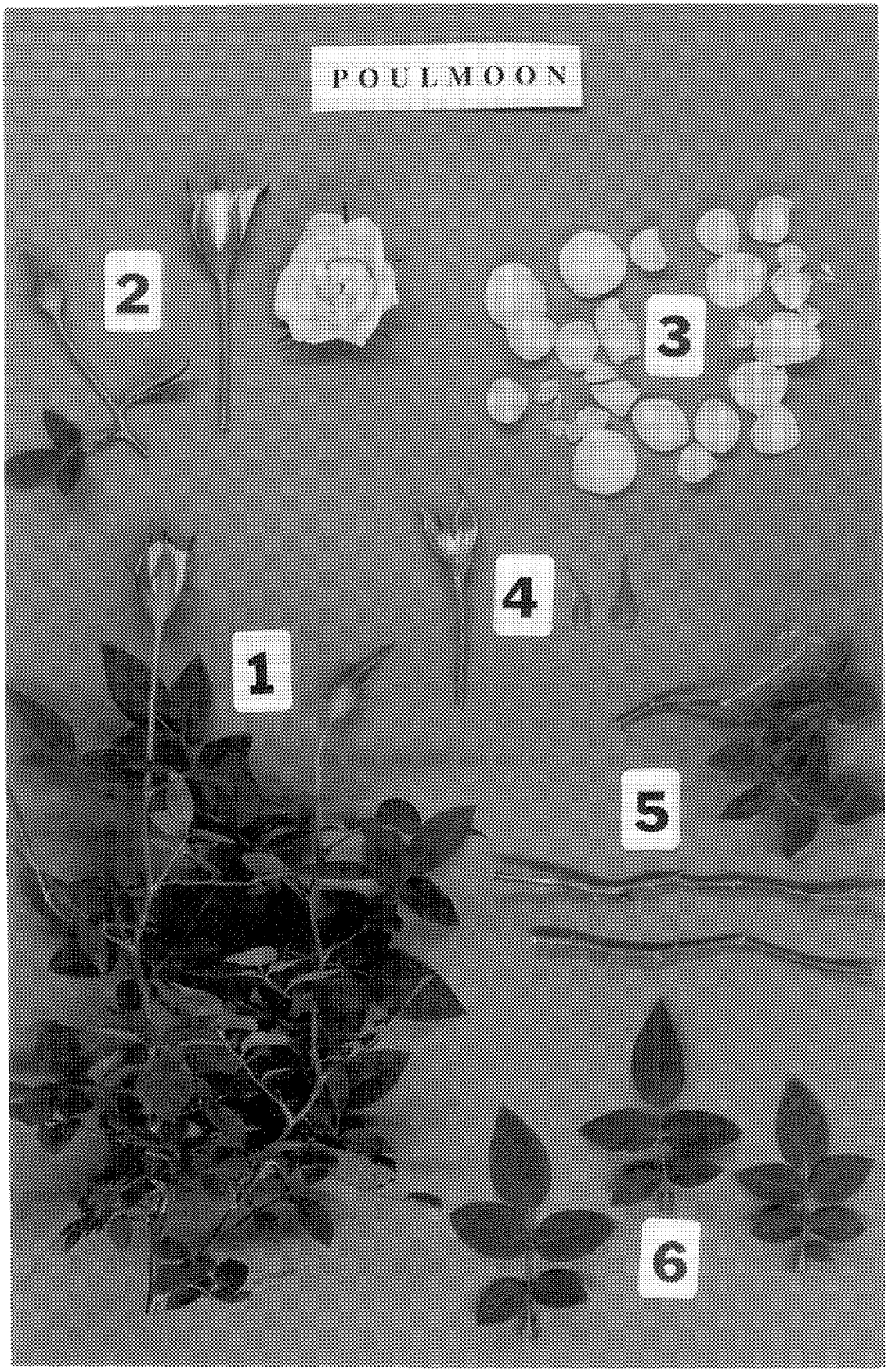
POULMOON
2
3
4
1
5
6